United States Patent
Günzel et al.

(10) Patent No.: US 11,648,817 B2
(45) Date of Patent: May 16, 2023

(54) METHOD AND DEVICE FOR DETECTING ODOR IN A TRANSPORTATION VEHICLE

(71) Applicant: VOLKSWAGEN AKTIENGESELLSCHAFT, Wolfsburg (DE)

(72) Inventors: Thorben Günzel, Braunschweig (DE); Stephan Max, Gifhorn (DE)

(73) Assignee: VOLKSWAGEN AKTIENGESELLSCHAFT

( * ) Notice: Subject to any disclaimer, the term of this patent is extended or adjusted under 35 U.S.C. 154(b) by 303 days.

(21) Appl. No.: 16/522,750

(22) Filed: Jul. 26, 2019

(65) Prior Publication Data

US 2020/0039318 A1    Feb. 6, 2020

(30) Foreign Application Priority Data

Jul. 31, 2018  (DE) ...................... 10 2018 212 800.6

(51) Int. Cl.
*B60H 1/00*       (2006.01)
*G01N 33/00*      (2006.01)
(Continued)

(52) U.S. Cl.
CPC ......... *B60H 1/008* (2013.01); *B60H 1/00771* (2013.01); *B60H 1/00849* (2013.01); *G01N 33/0075* (2013.01); *G01C 21/3697* (2013.01)

(58) Field of Classification Search
None
See application file for complete search history.

(56) References Cited

U.S. PATENT DOCUMENTS

2007/0041865 A1 *  2/2007  Ayoub .................... A61L 9/125
                                                          700/285
2010/0088016 A1    4/2010  Aghara et al.
(Continued)

FOREIGN PATENT DOCUMENTS

CN      105143827 A     12/2015
DE   102008039088 A1     2/2010
(Continued)

OTHER PUBLICATIONS

Batterman, Stuart et al. "High resolution spatial and temporal mapping of traffic-related air pollutants." International journal of environmental research and public health vol. 12,4 3646-66. Apr. 1, 2015, doi:10.3390/ijerph120403646 (Year: 2015).*

(Continued)

*Primary Examiner* — Aniss Chad
*Assistant Examiner* — Madison R Hughes
(74) *Attorney, Agent, or Firm* — Barnes & Thornburg, LLP

(57) ABSTRACT

A method and a device for detecting odor nuisances along a route of a subject transportation vehicle and for predictively initiating measures for preventing the penetration of the odorants of the odor nuisance into the subject transportation vehicle during travel. The method includes collecting swarm data from a plurality of swarm transportation vehicles in the surroundings of the route of the subject transportation vehicle, relating to the odor nuisance of each swarm transportation vehicle, ascertaining locations of an odor nuisance from the collected swarm data, ascertaining the extent of the odor nuisance around the respective location of the odor nuisance, and initiating measures in the subject transportation vehicle when approaching the location of an odor nuisance while taking into account the extent of the odor nuisance along the future route, wherein the measure is (Continued)

implemented at a predefined distance from the extent of the odor nuisance.

14 Claims, 1 Drawing Sheet

(51) Int. Cl.
*G01C 21/36* (2006.01)
*G08G 1/01* (2006.01)

(56) References Cited

U.S. PATENT DOCUMENTS

| | | |
|---|---|---|
| 2011/0084824 A1 | 4/2011 | Tewari et al. |
| 2016/0080160 A1 | 3/2016 | Venkataswami et al. |
| 2016/0280160 A1* | 9/2016 | MacNeille ............. G05B 15/02 |
| 2017/0369168 A1* | 12/2017 | Hwang ..................... A61L 9/14 |
| 2018/0334013 A1* | 11/2018 | Koravadi ............... B60H 1/008 |
| 2019/0084369 A1* | 3/2019 | Duan ................. B60H 1/00771 |
| 2019/0308487 A1* | 10/2019 | Badger, II ................ G07C 5/08 |

FOREIGN PATENT DOCUMENTS

| | | | |
|---|---|---|---|
| DE | 102011055684 A1 | 5/2013 | |
| DE | 102013220595 A1 | 4/2015 | |
| DE | 102015007063 B3 | 7/2016 | |
| DE | 102016224378 A1 | 6/2018 | |
| EP | 3189993 A1 | 7/2017 | |
| JP | 2005206110 A | 8/2005 | |
| JP | 2014201085 A | 10/2014 | |
| JP | 2016137818 A * | 8/2016 | |
| JP | 2017052339 A | 3/2017 | |
| WO | WO-2010075874 A1 * | 7/2010 | ......... B60H 1/00849 |
| WO | 2017104927 A1 | 6/2017 | |

OTHER PUBLICATIONS

Office Action; Chinese Patent Application No. 201910700463.1; dated Aug. 23, 2022.

* cited by examiner

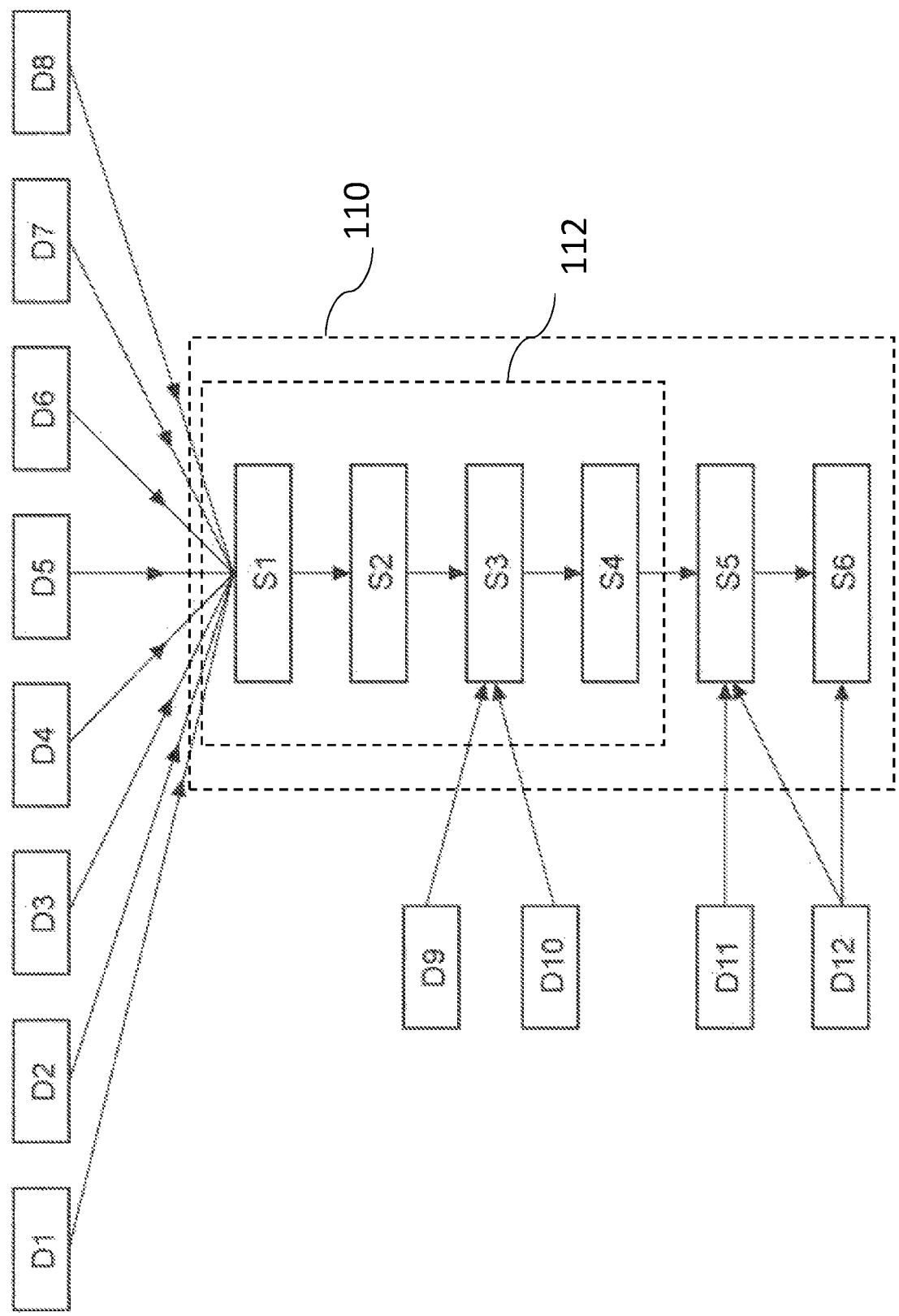

METHOD AND DEVICE FOR DETECTING ODOR IN A TRANSPORTATION VEHICLE

PRIORITY CLAIM

This patent application claims priority to German Patent Application No. 10 2018 212 800.6, filed 31 Jul. 2018, the disclosure of which is incorporated herein by reference in its entirety.

SUMMARY

Illustrative embodiments relate to a method for detecting odor nuisances along a route of a subject transportation vehicle and for predictively initiating measures for preventing the penetration of the odorants of the odor nuisance into the subject transportation vehicle and to a corresponding device.

BRIEF DESCRIPTION OF THE DRAWINGS

A disclosed embodiment is explained below with reference to the drawings, in which:

FIG. 1 shows a method for detecting the locations of unpleasant odors or odor nuisances and their remedy and/or prevention in the individual transportation vehicle.

DETAILED DESCRIPTION

Document JP 2017 052 339 A discloses a transportation vehicle apparatus having a communication apparatus which communicates in a wireless state with other transportation vehicles in the surroundings and acquires odor information including at least the position information of the odor from the transportation vehicles in the surroundings, and stores the odor information in a database. The transportation vehicle apparatus transmits the odor information stored in the database to the transportation vehicles in the surroundings using the communication apparatus. The air conditioning system predicts the positions, by which the subject transportation vehicle plans its route on the basis of the direction of travel which can be derived from the positions already traveled through and from the navigation system, and ascertains whether the odor information is present in the surroundings of the predicted transportation vehicle position or not. If the odor information is present in a positive sense, the transportation vehicle apparatus switches the air conditioning system from the external air mode to the recirculation mode.

Document US 2011/0084824 A1 describes a method for estimating the degree to which the occupants of a transportation vehicle are subjected to the ambient conditions, to subject the transportation vehicle occupants to the lowest loading. The occupants are warned about a zone with challenging environmental conditions, and the details of the environmental conditions and the duration of the exposure are communicated to the transportation vehicle occupants. In addition, a procedure as to how the environmental conditions can be countered is suggested to the transportation vehicle occupants, wherein it is also possible for such measures to occur automatically. The environmental conditions include, inter alia, fumes or dust, demanding weather conditions and/or emissions of odors.

Document DE 10 2011 055 684 A1 describes a method for operating a ventilation apparatus of a transportation vehicle, in which automatic activation of the ventilation apparatus occurs if a defined travel situation, such as, for example, a traffic jam, is present. However, the detection of a situation usually occurs only when the transportation vehicle is already in the corresponding situation and therefore the unpleasant odors are then already in the passenger compartment of the transportation vehicle. The recirculation mode is then no longer helpful.

Document DE 10 2008 039 088 A1 discloses controlling a ventilation apparatus as a function of the geographic position of the transportation vehicle to activate the recirculation mode of the ventilation apparatus of the transportation vehicle before entering into a tunnel. Since the detection is based on geographic positions of tunnels, the method is unsuitable for changing situations.

DE 10 2015 007 063 B3 discloses a method for producing a recirculation function profile of the road network in which the transportation vehicle-opposition-dependent or route-dependent activation of a recirculation function of ventilation apparatuses is made available to other transportation vehicles. In this context, the detection of the surrounding situation is based exclusively on the manual activation of the recirculation function, and in unpredictable situations the method is unsuitable, since the odors in the surroundings have already penetrated the interior of the transportation vehicle. Therefore, the recirculation mode is not activated and the transportation vehicle is ventilated to remove the odors from the transportation vehicle.

Document DE 10 2016 224 378 A1 describes a method for monitoring a sensor function of a sensor in a subject transportation vehicle. The method comprises comparing sensor data of the sensor with comparison data of a comparison sensor which is located outside the subject transportation vehicle, wherein the sensor data are acquired in a current position of the subject transportation vehicle, and the comparison data are acquired while the comparison sensor is located in a predefined region around the current position, and the assessment of the sensor function as a function of a comparison result of the sensor data with the comparison data.

The explained methods therefore have considerable weaknesses. There are therefore situations in which unpleasant odors enter the interior of the transportation vehicle without it being possible to predict this in advance. This is the case, for example, when traveling past roadworks involving the application of tar, when traveling past an agricultural area to which fertilizer has recently been applied or when traveling past certain gastronomic businesses.

In such situations, it would be possible to prevent the penetration of unpleasant odors into the interior of the transportation vehicle if the recirculation mode had been activated before the transportation vehicle travels past. However, if the unpleasant odor has already entered the interior of the transportation vehicle, the recirculation mode is no longer helpful and the interior of the transportation vehicle has to be ventilated with fresh air. This can ideally be carried out by intensive periodic ventilation by opened windows, a fresh air supply by a transportation vehicle ventilation apparatus or spraying odorants in the passenger compartment of the transportation vehicle when one has moved away from the location of the unpleasant odors.

Disclosed embodiments provide a method and a device with which odor nuisances along a predefined route can be detected and corresponding measures can be taken.

The is achieved by a method for detecting odor nuisances along a route of a subject transportation vehicle and for predictively initiating measures for preventing the penetration of odorants of the odor nuisance into the subject transportation vehicle and by a corresponding device.

The disclosed method for detecting odor nuisances along a router of a subject transportation vehicle and for predictively initiating measures for preventing the penetration of the odorants of the odor nuisance into the subject transportation vehicle during travel comprises:

collecting swarm data from a plurality of swarm transportation vehicles in the surroundings of the route of the subject transportation vehicle, relating to the odor nuisance of each swarm transportation vehicle, ascertaining locations of an odor nuisance from the collected swarm data, ascertaining the extent of the odor nuisance around the respective location of the odor nuisance, and initiating measures in the subject transportation vehicle when approaching the location of an odor nuisance while taking into account the extent of the odor nuisance along the future route, wherein the measure is implemented at a predefined distance from the extent of the odor nuisance.

In this way, locations and their surroundings at which unpleasant odors are present in a way which cannot be predicted are reliably detected and corresponding measures are taken, such as, for example, the automatic activation of the recirculation mode in transportation vehicles before these locations are passed.

The measure in the subject transportation vehicle may be cancelled when the subject transportation vehicle has traveled a predefined distance from the extent around the location of the odor nuisance. In this way, no one in the transportation vehicle has to be concerned with the fact that the ventilation of the transportation vehicle occurs with air from the outside, since an excessively long recirculation operation would reduce the air quality in the interior of the transportation vehicle.

Further, after the second operation of "ascertaining locations of an odor nuisance", an operation in which the plausibility of the locations of an odor nuisance is checked on the basis of map data and traffic information is inserted.

Between the operation of "ascertaining the extent of the odor nuisance around the ascertained location of the odor nuisance" and the operation of "initiating measures" an intermediate operation is inserted in which, as a function of the external temperature of the surroundings of the subject transportation vehicle and/or the climate in the transportation vehicle it is ascertained whether the initiation of measures is permissible.

The measures may consist in informing the driver and/or in activating an automatic activation of the recirculation mode of the ventilation system of the transportation vehicle. In the first case, it is left to the driver whether he activates the recirculation air before passing the odor nuisance, while in the second case, which can also be connected to a message, the recirculation air is activated automatically so that the driver probably does not notice the automatic measure if a message is not simultaneously issued.

The swarm data of a swarm transportation vehicle may comprise at least the speed of the swarm transportation vehicle, data of an odor nuisance in the surroundings of the swarm transportation vehicle, GPS data of the swarm data and route information of the swarm transportation vehicle. By this fundamental data, the location of an odor nuisance and its extent can be detected, so that the subject transportation vehicle and other transportation vehicles can be correspondingly instructed.

The predefined distance is also in the region of 1000 m on freeways, in the region of 500 m on country roads and in the region of 100 m on urban roads. Region in this context means that the deviation from the specified value is +/−10%.

The operations can also be carried out completely in the subject transportation vehicle or in a control center. It is also possible for the first four operations of which the location of the odor nuisance and its extent are carried out in a control center, and the following operations, which relate to the measures in the transportation vehicle, to be carried out in the subject transportation vehicle.

The disclosed device for detecting odor nuisances along a route of a subject transportation vehicle and for predictively initiating measures for preventing the penetration of the odorants of the odor nuisance into the subject transportation vehicle during travel, wherein the device for carrying out the method according of the preceding claims is constructed and configured comprises:

an apparatus for collecting swarm data from a plurality of swarm transportation vehicles in the surroundings of the route of the subject transportation vehicle, relating to the odor nuisance of each swarm transportation vehicle, an apparatus for ascertaining locations of an odor nuisance from the collected swarm data, an apparatus for ascertaining the extent of the odor nuisance around the respective location of the odor nuisance, and an apparatus for initiating and canceling measures in the subject transportation vehicle when approaching the location of an odor nuisance while taking into account the extent of the odor nuisance along the future route, wherein the measure is implemented at a predefined distance from the extent of the odor nuisance.

In addition, the device can have an apparatus for checking the plausibility of the locations of an odor nuisance on the basis of map data and traffic information.

The essential concept of the method consists in reliably detecting locations at which unpleasant odors, that is to say an odor nuisance, which cannot be predicted, are present, and in taking corresponding measures in the individual transportation vehicle, that is to say the subject transportation vehicle, such as, automatically activating the recirculation mode in transportation vehicles before these locations of the odor nuisances are passed, and of automatically deactivating the recirculation mode again after these locations are passed, wherein, under certain circumstances, it is necessary to close opened transportation vehicle windows before the recirculation mode is activated.

To be able to react correspondingly with suitable measures in an individual transportation vehicle, that is to say a subject transportation vehicle, during travel to locations or areas of odor nuisances, at least the following operations are carried out, wherein in the following example both the ascertaining and the processing of the swarm data and the execution of the measures in the subject transportation vehicle can be carried out by control center, for example, a back end computer, or all the operations can be carried out by a suitable controller in a subject transportation vehicle. It is also possible for the operations to be partially carried out in a control center and partially in the subject transportation vehicle. In addition, all the operations do not necessarily have to be carried out.

In a first operation at S1, swarm data are collected. In this context, the swarm data are collected from a plurality of transportation vehicles, referred to below as swarm transportation vehicles, during the current travel on different sections of routes, and are transmitted, for example, to the control center. The swarm data are to be understood as a plurality of data items which are transmitted by a swarm transportation vehicle, wherein the swarm data include the speed D1 of a swarm transportation vehicle, the occurrence of an odor nuisance in the surroundings of the swarm transportation vehicle or the feeding of odorants D2 into the swarm transportation vehicle, the open state of windows D3 of the swarm transportation vehicle, GPS data D4 of the swarm transportation vehicle, the operating state of the air conditioning system D5 of the swarm transportation vehicle, the operating state of the ventilation system D6 of the swarm transportation vehicle, the external temperature D7 of the surroundings of the swarm transportation vehicle and the route information D8 of the navigation system of the swarm transportation vehicle. In addition, the corresponding data the subject transportation vehicle are also involved in the formation of the swarm data. In other words, the data of the subject transportation vehicle are included in the totality of the swarm data and are taken into account.

It is also possible for the subject transportation vehicle to receive the swarm data from swarm transportation vehicles in the further surroundings and to evaluate the data independently. The occurrence of an odor nuisance or the feeding of odorants into the swarm transportation vehicle can be ascertained by a suitable analysis apparatus which responds to corresponding odorants and which can be arranged in a suitable way on the swarm transportation vehicle, for example, in the fresh air supply or at another suitable location so that the odors and their load can be determined outside the swarm transportation vehicle. It is also possible that when an odor nuisance occurs the drivers swarm transportation vehicles pass it on manually, as it were, make it available online.

In a second operation at S2, locations of unpleasant odors or odor nuisances which can be predicted from the swarm data are ascertained. This ascertaining process is carried out by evaluating the swarm data D1 to D8 which are received in the first operation at S1. The enumeration of the swarm data is not to be understood as conclusive and further data such as, for example, environmental data or weather data can be included in the evaluation. A suitable selection of the swarm data can be used for the evaluation.

In the third operation at S3, which is optional, plausibility of the ascertained locations are checked on the basis of digital map data D10 and/or online traffic data D9. It is therefore possible infer, for example, the presence of agricultural fields in the vicinity of the ascertained location or a gastronomic activity from the map data D10. For example, the presence of roadworks, which could form an odor nuisance when tar is being applied, can be detected, from the traffic information D9.

In the fourth operation at S4, the extent of the location which has been noticed through unpleasant odors in the evaluation performed in the second operation at S2 is ascertained. This can be done, for example, by the evaluation of opposing directions of travel in operation at S2 and/or by including map data from the optional operation at S3 and/or by assumptions with respect to the possibly affected section of route.

In the fifth operation at S5, the driver is informed about the odor nuisance to be expected, or automatic activation of the recirculation mode of the ventilation system takes place. Both the informing of the driver and the automatic switching over of the recirculation mode occurs as a function of the distance of the transportation vehicle from the ascertained location of the odor nuisance and, under certain circumstances, of the route from the navigation device. In this context, the recirculation mode is activated at a predefined distance before the ascertained location of the odor nuisance is reached, to ensure that no odors pass into the passenger compartment of the subject transportation vehicle. In this context, data D11 relating to the route present in the navigation of the subject transportation vehicle and GPS data D12 of the subject transportation vehicle are also included.

In the sixth operation at S6, the recirculation mode is deactivated automatically if the recirculation mode has been activated automatically and the transportation vehicle has moved away by at least a predefined distance from the location of the odor nuisance including the extent of the location. Alternatively, the deactivation of the recirculation mode can also be controlled intelligently on the basis of the knowledge from the swarm data D1 to D8. In this context, the predefined distance can also a function of the type of road on which the transportation vehicle is moving. Therefore, for example, for the operations at S5 and S6 the predetermined distance can be 1000 m on a freeway, 500 m on a country road and 100 m in an urban area, wherein a region of 10% around the specified distances is postulated as a fluctuation width. GPS data D4 are also included in this operation at S6.

In addition, another intermediate operation, in which it is tested whether the activation of the recirculation mode as a function of the external temperature D7 and the climate D5 in the passenger compartment of the transportation vehicle is permissible can also be inserted between the operations at S4 and S5.

As already mentioned, the operations at S1 to S6 can be carried out completely in the subject transportation vehicle. However, it is also possible to carry out the totality of the operations in a control center, for example, a backend computer, or the operations at S1 to S4 are ascertained in the control center and the subject transportation vehicle retrieves the information corresponding to its future route from the control center and carries out operations at S5 and S6 in the subject transportation vehicle.

As already mentioned, the operations at S1 to S6 can be carried out completely in the subject transportation vehicle. However, it is also possible to carry out the totality of the operations in a control center 110, for example, a backend computer 112, or the operations at S1 to S4 are ascertained in the control center 110 and the subject transportation vehicle retrieves the information corresponding to its future route from the control center 110 and carries out operations at S5 and S6 in the subject transportation vehicle.

LIST OF REFERENCE SYMBOLS

D1 Transportation vehicle speed
D2 Feeding of odorants into the interior of the transportation vehicle
D3 Open state of transportation vehicle windows
D4 GPS data of swarm transportation vehicle
D5 Operating state of air conditioning system
D6 Operating state of ventilation system
D7 External temperature
D8 Route information of swarm transportation vehicle
D9 Traffic information
D10 Map data
D11 Route information and navigation of subject transportation vehicle
D12 GPS data of subject transportation vehicle
S1 Collecting of swarm data
S2 Ascertaining of predictable locations of unpleasant odors S3 Plausibility checking based on map data and traffic information S4 Ascertaining the extent of the location of the unpleasant odors S5 Automatic activation of the recirculation mode S6 Automatic deactivation of the recirculation mode

The invention claimed is:

1. A non-transitory, computer readable medium, implementing a method for detecting a plurality of odor nuisances along a route of a subject transportation vehicle and for predictively initiating and canceling measures for preventing penetration of odorants of the plurality of odor nuisances into the subject transportation vehicle during travel, the method comprising:

collecting swarm data from a plurality of swarm transportation vehicles in the surrounding area of the route of the subject transportation vehicle, the swarm data relating to one or more odor nuisances detected by each swarm transportation vehicle;

ascertaining, from the collected swarm data, respective locations of each odor nuisance detected by each swarm transportation vehicle;

ascertaining an extent of each odor nuisance around the respective location of each odor nuisance; and initiating the measures in the subject transportation vehicle when approaching at least one respective location of a particular odor nuisance while taking into account the extent of the particular odor nuisance along a future portion of the route, wherein the measures are implemented at a predefined distance from the extent of the particular odor nuisance, wherein the measures in the subject transportation vehicle are cancelled in response to the subject transportation vehicle having traveled the predefined distance from the extent of the particular odor nuisance, and wherein areas of dense traffic are identified as locations of odor nuisance, wherein the predefined distance is a first predefined distance when the subject transportation vehicle is travelling on freeways, a second predefined distance when the subject transportation vehicle is travelling on country roads, and a third predefined distance when the subject transportation vehicle is travelling on urban roads.

2. The non-transitory, computer readable medium of claim 1, wherein, between ascertaining of the respective locations of each odor nuisance and initiating the measures, a determination is made whether to initiate the measure, and the determination is based on the external temperature of the surroundings of the subject transportation vehicle and/or the climate in the subject transportation vehicle.

3. The non-transitory, computer readable medium of claim 1, wherein the measures include informing a driver and/or activating a recirculation air mode of a ventilation system of the subject transportation vehicle.

4. The non-transitory, computer readable medium of claim 1, wherein the swarm data of a particular swarm transportation vehicle comprises at least the speed of the particular swarm transportation vehicle, data about odor nuisance in the surroundings of the particular swarm transportation vehicle, GPS data of the particular swarm transportation vehicle and route information of the particular swarm transportation vehicle.

5. The non-transitory, computer readable medium of claim 1, wherein collecting swarm data, and ascertaining respective locations of each odor nuisance are performed in a control center separate from the subject transportation vehicle, whereas the initiation of measures in the subject transportation vehicle when approaching the location of the particular odor nuisance is performed in the subject transportation vehicle.

6. The method of claim 1, wherein the first predefined distance is 1000 meters, the second predefined distance is 500 meters, and the third predefined distance is 100 meters.

7. A method for detecting a plurality of odor nuisances along a route of a subject transportation vehicle and for predictively initiating and canceling measures for preventing penetration of odorants of the plurality of odor nuisances into the subject transportation vehicle during travel, the method comprising:

collecting swarm data from a plurality of swarm transportation vehicles in a surrounding area of the route of the subject transportation vehicle, the swarm data relating to one or more odor nuisances detected by each swarm transportation vehicle;

ascertaining, from the collected swarm data, respective locations of each odor nuisance detected by each swarm transportation vehicle;

ascertaining an extent of each odor nuisance around the respective location of each odor nuisance; and initiating the measures in the subject transportation vehicle when approaching at least one respective location of a particular odor nuisance while taking into account the extent of the particular odor nuisance along a future portion of the route, wherein the measures are implemented at a predefined distance from the extent of the particular odor nuisance, wherein the measures in the subject transportation vehicle are cancelled in response to the subject transportation vehicle having traveled the predefined distance from the extent of the particular odor nuisance, and wherein areas of dense traffic are identified as locations of odor nuisance, wherein the predefined distance a first predefined distance when the subject transportation vehicle is travelling on freeways, a second predefined distance when the subject transportation vehicle is travelling on country roads, and a third predefined distance when the subject transportation vehicle is travelling on urban roads.

8. The method of claim 7, wherein, between ascertaining the extent of each odor nuisance around the respective location of each odor nuisance, and initiating the measures in the subject transportation vehicle, a determination is made whether the initiation of measures is permissible based on the external temperature of the surroundings of the subject transportation vehicle and/or the climate in the subject transportation vehicle.

9. The method of claim 7, wherein the measures include informing a driver and/or activation of a recirculation air mode of a ventilation system of the subject transportation vehicle.

10. The method of claim 7, wherein the swarm data of a swarm transportation vehicle comprises at least the speed of the swarm transportation vehicle, data about odor nuisance in the surroundings of the swarm transportation vehicle, GPS data of the swarm transportation vehicle and route information of the swarm transportation vehicle.

11. The method of claim 7, wherein the method is performed in the subject transportation vehicle.

12. The method of claim 7, wherein the method is performed in the in a control center separate from the subject transportation vehicle.

13. The method of claim 7, wherein the collecting of swarm data, and ascertaining locations and extent of each odor nuisance are performed in a control center separate from the subject transportation vehicle, whereas initiating measures in the subject transportation vehicle when approaching at least one respective location of the particular odor nuisance is performed in the subject transportation vehicle.

14. The method of claim 7, wherein the first predefined distance is 1000 meters, the second predefined distance is 500 meters, and the third predefined distance is 100 meters.

\* \* \* \* \*